(12) United States Patent
Parayil et al.

(10) Patent No.: US 10,927,067 B2
(45) Date of Patent: Feb. 23, 2021

(54) ORGANIC CRYSTALLINE SALT OF HALOACETIC ACID

(71) Applicants: Sarin Parayil, Thane (IN); Anil Roy, Hyderabad (IN)

(72) Inventors: Sarin Parayil, Thane (IN); Anil Roy, Hyderabad (IN)

( * ) Notice: Subject to any disclaimer, the term of this patent is extended or adjusted under 35 U.S.C. 154(b) by 0 days.

(21) Appl. No.: 16/464,628

(22) PCT Filed: Nov. 28, 2017

(86) PCT No.: PCT/IB2017/057431
§ 371 (c)(1),
(2) Date: May 28, 2019

(87) PCT Pub. No.: WO2018/096517
PCT Pub. Date: May 31, 2018

(65) Prior Publication Data
US 2020/0039919 A1    Feb. 6, 2020

(30) Foreign Application Priority Data

Nov. 28, 2016 (IN) .............................. 201621040455

(51) Int. Cl.
*C07C 215/12* (2006.01)
*C07C 53/16* (2006.01)

(52) U.S. Cl.
CPC ............ *C07C 215/12* (2013.01); *C07C 53/16* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 5,554,789 A | 9/1996 | Carganico et al. | |
| 2003/0013764 A1 | 1/2003 | Constantin-Teodosiu et al. | |
| 2005/0153939 A1* | 7/2005 | Venit ..................... | A61K 9/28 514/114 |
| 2009/0156620 A1* | 6/2009 | Sharp ..................... | A61P 9/00 514/266.24 |
| 2012/0059033 A1* | 3/2012 | Yang ..................... | A61P 31/12 514/312 |

FOREIGN PATENT DOCUMENTS

| | | |
|---|---|---|
| EP | 2711373 B1 | 11/2017 |
| JP | 2014519475 A | 8/2014 |
| WO | 2015135926 A1 | 9/2015 |

OTHER PUBLICATIONS

International Search Report and Written Opinion of International Application No. PCT/IB2017/057431, dated Mar. 23, 2018, 9 pp.
International Preliminary Report on Patentability from International Application No. PCT/IB2017/057431, dated May 28, 2019, 7 pp.

* cited by examiner

*Primary Examiner* — Clinton A Brooks
*Assistant Examiner* — Jennifer C Sawyer
(74) *Attorney, Agent, or Firm* — Shumaker & Sieffert, P.A.

(57) ABSTRACT

The present invention specifically relates to novel salt and crystalline form of haloacetic acid and its process of preparation. The invention more particularly relates to novel crystalline form dichloroacetate tromethamine salt and its process of preparation. The present invention more specifically relates to the dichloroacetate tromethamine salt, its process and its use for the treatment of various diseases and/or disorders.

4 Claims, 8 Drawing Sheets

ORGANIC CRYSTALLINE SALT OF HALOACETIC ACID

This application is a national stage application under 35 U.S.C. § 371 of PCT Application No. PCT/IB2017/057431, filed Nov. 28, 2017, which claims the benefit of IN Application No. 201621040455 filed Nov. 28, 2016. The entire contents of each of PCT Application No. PCT/IB2017/057431 and IN Application No. 201621040455 are incorporated herein by reference in their entirety.

FIELD OF INVENTION

The present invention specifically relates to novel salt of haloacetic acid and its process of preparation. The invention more particularly relates to novel crystalline salt of haloacetic acid. The invention more particularly relates to dichloroacetate tromethamine salt and its process of preparation.

The present invention more specifically relates to the novel crystalline form of dichloroacetate tromethamine salt and process for its preparation.

The present invention also relates to the co-crystal of dichloroacetate with tromethamine and process for its preparation.

The present invention also relates to the use of novel salt of dichloroacetate tromethamine for the treatment of various diseases and/or disorders.

BACKGROUND OF INVENTION

Haloacetic acids were first detected in 1983 as disinfection by-products in chlorinated drinking-waters, 9 years after the discovery of trihalomethanes in chlorinated waters. Dichloroacetic acid was reported to be first synthesized in 1864 by the further chlorination of monochloroacetic acid with chlorine and was mostly used for industrial purposes and clinical trials were started as early as 1990 to look at DCA use in children with lactic acidosis.

Dichloroacetic Acid (DCA), also known as dichloroethanoic acid, is an analogue of acetic acid in which two of the three hydrogen atoms of the methyl group have been replaced by Chlorine atoms. The chemical formula is $C_2H_2Cl_2O_2$, the molecular weight is 128.94 and the structural formula is:

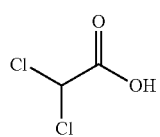

(V)

Dichloroacetic acid was reported to be first synthesized in 1864 by the further chlorination of monochloroacetic acid with chlorine. The most common production method for dichloroacetic acid is the hydrolysis of dichloroacetyl chloride, which is produced by the oxidation of trichloroethylene. It can also be obtained by hydrolysis of pentachloroethane with 88-99% sulfuric acid or by oxidation of 1,1-dichloroacetone with nitric acid and air. In addition, dichloroacetic acid can be produced by catalytic dechlorination of trichloroacetic acid or ethyl trichloroacetate with hydrogen over a palladium catalyst.

Dichloroacetic acid is available in liquid form and the sodium and potassium salt of dichloroacetic acid is available in powder form. Specific pharmaceutical salts reported and used for various clinical investigations include sodium dichloroacetate, potassium dichloroacetate, and diisopropyl ammonium dichloroacetate. The sodium dichloroacetate and free base forms are highly reported and used. These salts of DCA have been studied as potential drugs because they inhibit the enzyme pyruvate dehydrogenase kinase. DCA have been studied as potential treatment for cancer, lactic acidosis, congenital lactic acidosis, lactic acidosis in patients with severe malaria, pulmonary hypertension, diabetes, cholesterol lowering, homozygous familial hypercholesterolemia, severe head injury, systemic monochloroacetic acid poisoning and post-ischemic recovery.

Tromethamine (Tris, or tris(hydroxymethyl)aminomethane, or THAM) is an organic amine buffer approved for treating systemic acidosis where bicarbonate buffer is not recommended. Tromethamine is an approved drug and is used as an alternative to sodium bicarbonate in the treatment of metabolic acidosis. Tromethamine is also used as a base component for making salts which are used as pharmaceutical active agents. The chemical name of Tromethamine is 2-amino-2-(hydroxymethyl)-1,3-propanediol and the structural formula is: (Source: US label of THAM)

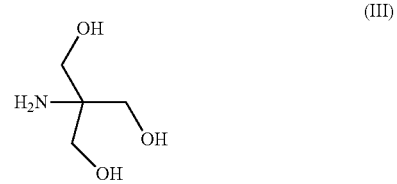

(III)

Tromethamine has remarkable advantages both from the physical and chemical point of view, compared with the commonly used amines, such as triethanolamine and diethanolamine. As far as its physical-chemical characteristics are concerned, tromethamine is a weakly basic polar amine (pKb=7.8) which forms buffer solutions of about the plasma pH, therefore it is also used as isotonic solution and to control the body and blood pH during transfusions. Tromethamine reduces or removes any risk of formation of carcinogenic nitrosoamines in that, being it a primary amine, it forms unstable nitrosoamines, which decompose in the presence of the nitrosating agent. Moreover, tromethamine itself is used as a medicament in respiratory and metabolic acidosis syndromes. This drug reacts with carbonate ion present in blood circulation and in this way it enhances the bicarbonate ion concentration. It is not intended to neutralize hydrogen ion in cells directly. Its lactic acid neutralising property makes it a preferred choice for treatment of metabolic acidosis, metabolic disorder and cancers.

Dichloroacetate lowers lactate due to inhibition of pyruvate dehydrogenase kinase and reduces lactic acid production by cells and Tromethamine being physiological buffer neutralizes already generated and circulating physiological lactic acid which enhances its clinical efficacy due to synergistic action as both compound acts on physiological lactate lowering mechanism inhuman and animal.

US 2003/0013764 disclose use of Dichloroacetic acid and its salts to prepare a medicament for the treatment of ischaemia in limbs.

WO 2015/135926 discloses tromethamine salt Dichloroacetic acid generically for treating a disease caused by a glycolytic parasite in a mammal. However, there is no specific disclosure related to Dichloroacetate tromethamine salt.

None of the prior art references discloses the tromethamine salt of haloacetic acid, tromethamine salt of dichloroacetic acid, specifically crystalline form of dichloroacetate tromethamine salt and its process of preparation.

The present invention provides the novel salt of haloacetic acid, tromethamine salt of haloacetic acid, tromethamine salt of dichloroacetic acid which is clear white crystals with specified dimension, very stable, water soluble and overcomes hygroscopicity problem of existing sodium and potassium salts of dichloroacetic acid.

OBJECTIVE OF INVENTION

The objective of the present invention is to provide novel salt of haloacetic acid.

Another objective of the present invention to provides process for the preparation of novel salt of haloacetic acid.

Still another objective of the present invention is to provide dichloroacetate tromethamine salt.

Another objective of the present invention is to provide process for the preparation of dichloroacetate tromethamine salt.

Another objective of the present invention is to provide novel crystalline form of dichloroacetate tromethamine salt.

Another objective of the present invention to provides process for the preparation of novel crystalline form of dichloroacetate tromethamine salt.

Another objective of the present invention to provides co-crystals of dichloroacetate tromethamine.

Yet another objective of the present invention is to provide the use of novel salt of dichloroacetate tromethamine for the treatment of various diseases and/or disorders.

Still another objective of the present invention is to provide stable, water soluble white crystals of dichloromethane tromethamine which overcomes hygroscopicity problem of existing sodium and potassium salts of dichloroacetic acid.

SUMMARY OF INVENTION

Accordingly, the present invention provides a novel tromethamine salt of haloacetic acid of Formula (I)

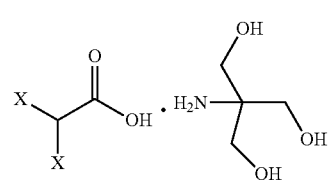

(I)

wherein X is selected from chloro, bromo, fluoro and iodo.

In a preferred aspect, the present invention provides a process for the preparation of tromethamine salt haloacetic acid of Formula (I)

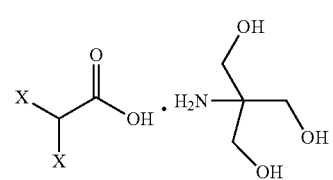

(I)

which comprises combining haloacetic acid of Formula (IV)

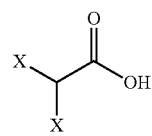

(IV)

and tromethamine of Formula (III) in water or organic solvent

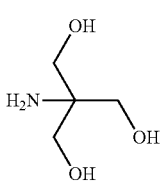

(III)

wherein X is selected from chloro, bromo, fluoro and iodo.

In another preferred aspect, the present invention provides a process for preparing haloacetic acid salt of Formula (I)

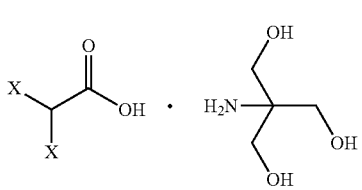

(I)

a) combining haloacetic acid and tromethamine in water or organic solvent,
b) stirring the reaction mixture of step (a) for 10 to 30 min at room temperature then heating the reaction mixture from step (b) at 50 to upto reflux temperature of the solvent to obtain haloacetic acid tromethamine salt,
c) isolating the haloacetic acid tromethamine salt,
d) drying the product.

In another preferred aspect, the present invention provides a process for the preparation of crystalline form of haloacetic acid salt of Formula (I)

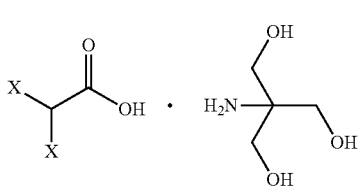

(I)

a) combining haloacetic acid and tromethamine in water or organic solvent,
b) stirring the reaction mixture of step (a) for 10 to 30 min at room temperature then cooling the reaction mixture from step (b) at <10° C. for more than 2 to 6 hours or longer to obtain pure and stable crystals. Salt precipitates as clear crystalline form,
c) isolating the crystalline form of haloacetic acid tromethamine salt,
d) drying the product.

The present invention provides novel tromethamine salt of dichloroacetic acid of Formula (II)

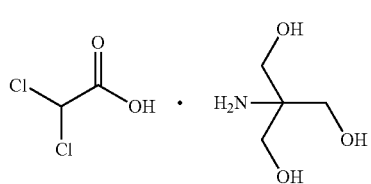
(II)

In a preferred aspect, the present invention provides a process for the preparation of novel tromethamine salt of dichloroacetic acid of Formula (II)

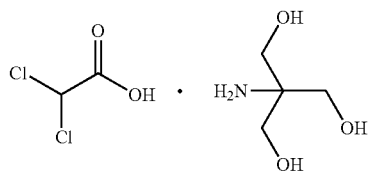
(II)

which comprises combining dichloroacetic acid of Formula (V)

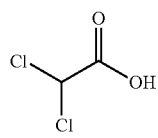
(V)

and tromethamine of Formula (III) in water or organic solvent.

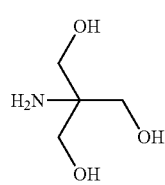
(III)

In another preferred aspect, the present invention provides a process novel tromethamine salt of dichloroacetic acid of Formula (II)

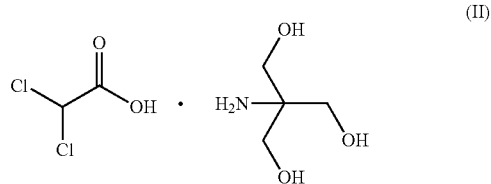 [SMILES: O=C(O)C(Cl)Cl ; NC(CO)(CO)CO]
(II)

a) combining dichloroacetic acid and tromethamine in water or organic solvent,
b) stirring the reaction mixture of step (a) for 10 to 30 min at room temperature then heating the reaction mixture from step (b) at 50 to upto reflux temperature of the solvent to obtain dichloroacetic acid tromethamine salt,
c) isolating the dichloroacetic acid tromethamine salt,
d) drying the product.

In another preferred aspect, the present invention provides crystalline form of dichloroacetate tromethamine salt of Formula (II).

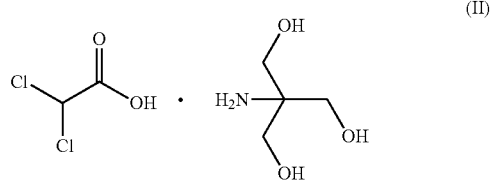 [SMILES: O=C(O)C(Cl)Cl ; NC(CO)(CO)CO]
(II)

In another preferred aspect, the present invention provides a process of crystalline form of dichloroacetate tromethamine salt of Formula (II)

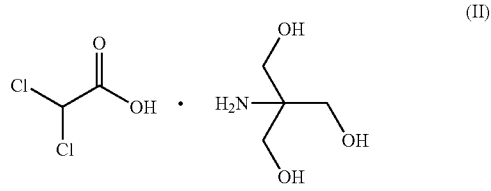 [SMILES: O=C(O)C(Cl)Cl ; NC(CO)(CO)CO]
(II)

a) combining dichloroacetic acid and tromethamine in water or organic solvent,
b) stirring the reaction mixture of step (a) for 10 to 30 min at room temperature then cooling the reaction mixture from step (b) at <10° C. for more than 2 to 6 hours or longer to obtain pure and stable crystals,
c) isolating the crystalline form of dichloroacetic acid tromethamine salt,
d) drying the product.

In another preferred aspect, the present invention provides co-crystal of dichloroacetate with tromethamine of Formula (VII).

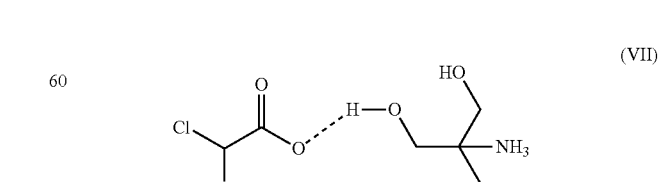
(VII)

In another preferred aspect, the present invention provides use of novel salt of dichloroacetate tromethamine for the treatment of various diseases and/or disorders.

In another preferred aspect, the present invention provides stable, water soluble white crystals of dichloromethane tromethamine which overcomes hygroscopicity problem of existing sodium and potassium salts of dichloroacetic acid.

DETAILED DESCRIPTION OF THE INVENTION

Figure 1:
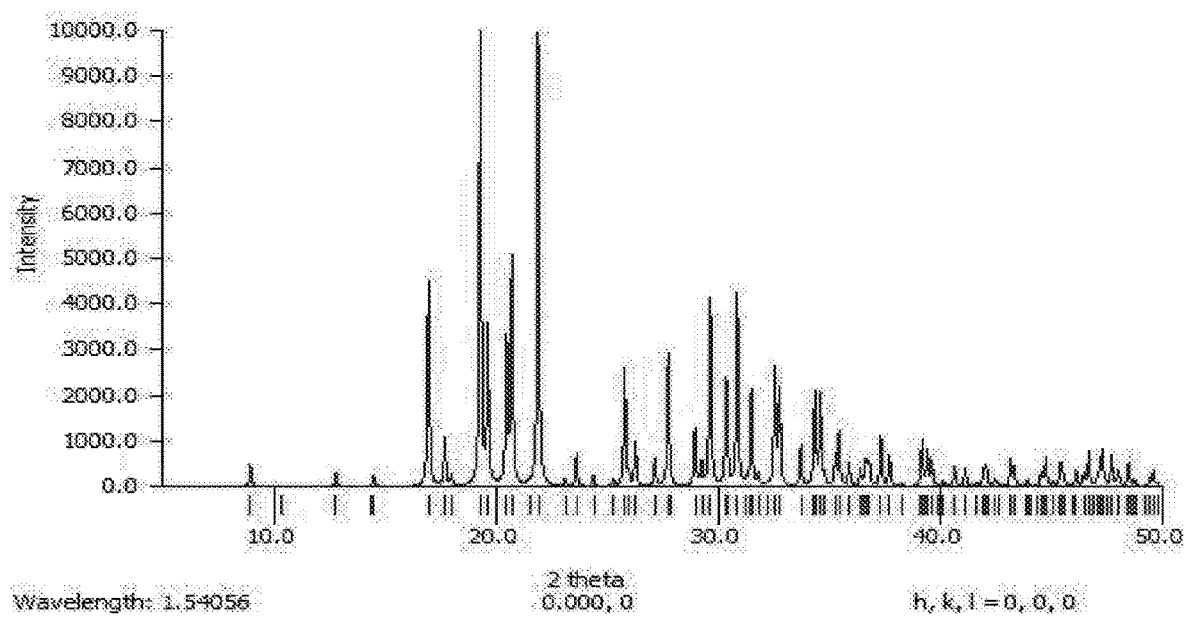
FIG. 1 shows Powder X-ray diffraction (PXRD) pattern of co-crystals of dichloroacetate tromethamine.

Accordingly, the present invention provides novel salt of haloacetic acid.

In one embodiment, the present invention provides process for the preparation of haloacetic acid salt of Formula (I).

In another embodiment, X in tromethamine salt haloacetic acid of Formula (I) represents chloro, bromo, fluoro and iodo.

In one embodiment, Formula (IV) is combined with Formula (III) in water or organic solvent to form Formula (I).

In one embodiment, Formula (V) is combined with Formula (III) in water or organic solvent to form Formula (II).

In one embodiment, organic solvents that may be used in the present invention include, but are not limited to water or deuterated water, alcohols such as methanol, ethanol, 1-propanol, 1-butanol, 2-butanol, t-butyl alcohol, 1-pentanol, 2-pentanol, 2-ethoxyethanol, ethylene glycol, glycerol, and the like; ketones such as acetone, butanone, 2-pentanone, 3-pentanone, methyl butyl ketone, methyl iso-butyl ketone, and the like; esters such as ethyl formate, methyl acetate, ethyl acetate, propyl acetate, t-butyl acetate, isobutyl acetate, methyl propanoate, ethyl proponoate, methyl butanoate, ethyl butanoate, and the like; ethers such as diethyl ether, diisopropyl ether, t-butyl methyl ether, dibutyl ether, tetrahydrofuran, 1,2-dimethoxyethane, 1,4-dioxane, 2-methoxyethanol, 2-ethoxyethanol, anisole, and the like; aliphatic and alicyclic hydrocarbons, unsubstituted and substituted, such as hexanes, n-heptane, n-pentane, cyclohexane, methylcyclohexane, nitromethane, and the like; halogenated hydrocarbons such as dichloromethane, chloroform, carbon tetrachloride, 1,1,2-trichloroethane, 1,2-dichloroethene, and the like; aromatic hydrocarbons such as toluene, xylenes, chlorobenzene, tetraline, and the like; nitriles such as acetonitrile, propionitrile, and the like; and any mixtures thereof. Preferably used organic solvents are ethanol, ether, acetone, carbon tetrachloride and deuterated water.

In another embodiment, reaction conditions used to form haloacetic tromethamine salt is heating the reaction mixture in the range of 50 to 70° C.

In another embodiment, the present invention provides novel crystalline form haloacetic acid tromethamine salt.

In one embodiment, the present invention provides process for the preparation of novel crystalline form haloacetic acid tromethamine salt.

In another embodiment, reaction conditions used to novel crystalline form haloacetic acid tromethamine salt is cooling the reaction mixture <10° C. for more than 2 to 6 hours or longer to obtain pure and stable crystals.

In another embodiment, the present invention provides novel tromethamine salt of dichloroacetic acid.

In another embodiment, reaction conditions used to form dichloroacetic tromethamine salt is heating the reaction mixture in the range of 50 to upto reflux temperature of the solvent.

In another embodiment, the present invention provides dichloroacetate tromethamine salt in the ratio of 1:1 to 1:3 of tromethamine and dichloroacetic acid.

In another embodiment, the present invention provides novel crystalline form of dichloroacetic acid tromethamine salt.

In another embodiment, the present invention provides novel crystalline form of dichloroacetic acid tromethamine salt in the ratio of 1:1 to 1:3 of tromethamine and dichloroacetic acid.

In another embodiment, the present invention provides co-crystal of dichloroaetate tromethamine in the ratio of 1:1 to 1:3 of tromethamine and dichloroacetic acid.

In another embodiment, elemental analysis for co-crystals of dichloroacetate tromethamine shows that C is found to be 28.72%, H is found to be 4.91% and N is found to be 5.34%.

In one embodiment, the present invention provides co-crystals of dichloroacetate tromethamine characterized by Powder x-ray diffraction pattern comprising diffraction peaks at 2θ values of 8.1, 12.8, 14.1, 17.1, 18.1, 19.1, 19.3, 21.2, 23.2, 24.5, 25.3, 26.0, 27.0, 28.0, 29.8, 30.2, 31.0, 34.0, 35.2, 36.0, 41.20, 42.0, 44.0 and 45.0±0.2 degrees 2 theta.

In one embodiment, the present invention provides co-crystals of dichloroacetate tromethamine characterized by single crystal X-ray data $C_6H_{13}Cl_2NO_5$ (M=250.07 g/mol): monoclinic, space group P2$_1$, a=8.600(2) Å, b=6.1391(15) Å, c=9.786(2) Å, α=90°, β=96.982(10°), γ=90°, V=512.8(2) Å$^3$, Z=2, T=297(2) K, μ(Mo Kα)=0.630 mm$^{-1}$, Dcalc=1.619 Mg/m$^3$, 12616 reflections measured (2.386≤2θ≤33.105°), 3782 unique ($R_{int}$=0.0216, $R_{sigma}$=0.0229). The final $R_1$ was 0.0175 (I>2σ(I)) and $wR_2$ was 0.0435 (all data).

In one embodiment, the present invention provides co-crystals of dichloroacetate tromethamine characterized by Powder X-ray diffraction (PXRD) pattern as shown in FIG. 1.

Figure 2:
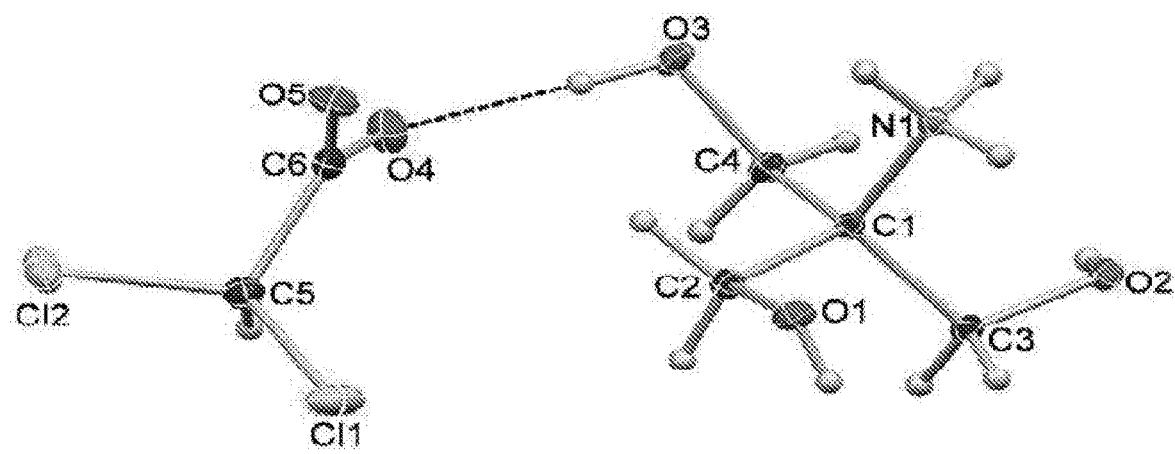
FIG. 2 shows the single crystal x-ray diffraction of co-crystals of dichloroacetate tromethamine.

In one embodiment, the present invention provides co-crystals of dichloroacetate tromethamine characterized by Single crystal X-ray diffraction as shown in FIG. 2.

Figure 3:
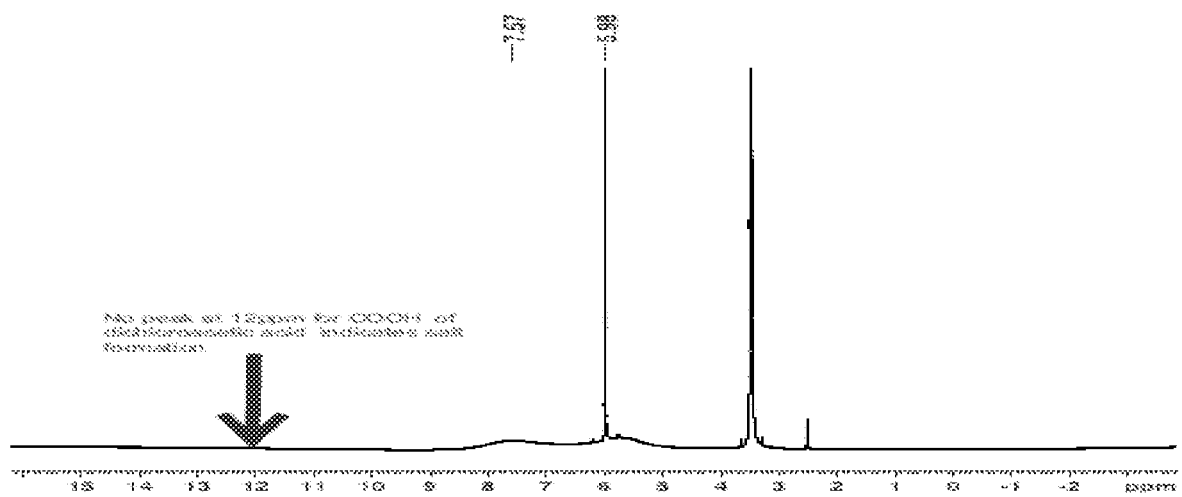
FIG. 3 shows $^1$H NMR of co-crystals of dichloroacetate tromethamine.

In another embodiment, the present invention provides co-crystals of dichloroacetate tromethamine characterized by proton NMR as shown in FIG. 3.

Figure 4:
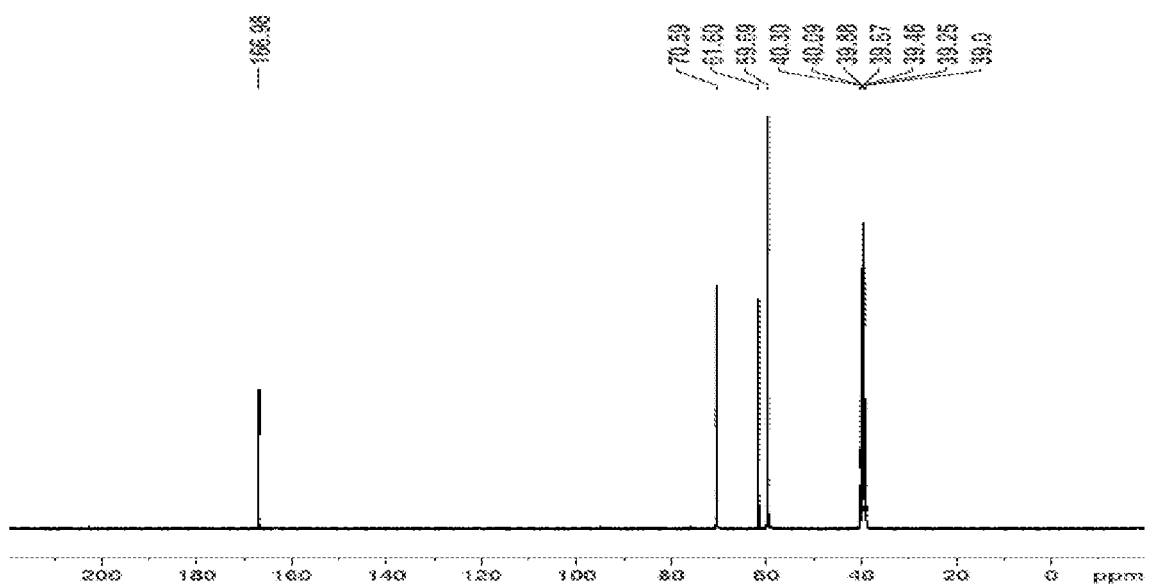
FIG. 4 shows $^{13}$C NMR of co-crystals of dichloroacetate tromethamine.

In another embodiment, the present invention co-crystals of dichloroacetate tromethamine characterized by $^{13}$C NMR as shown in FIG. 4.

Figure 5:
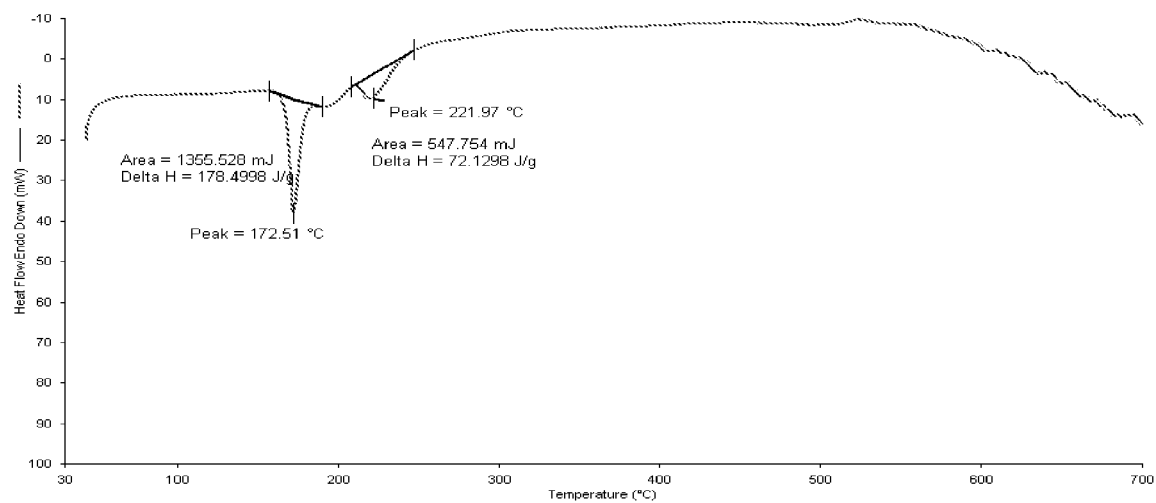
FIG. 5 shows DSC of co-crystals of dichloroacetate tromethamine.

In another embodiment, the present invention provides co-crystals of dichloroacetate tromethamine characterized by DSC as shown in FIG. 5.

Figure 6:
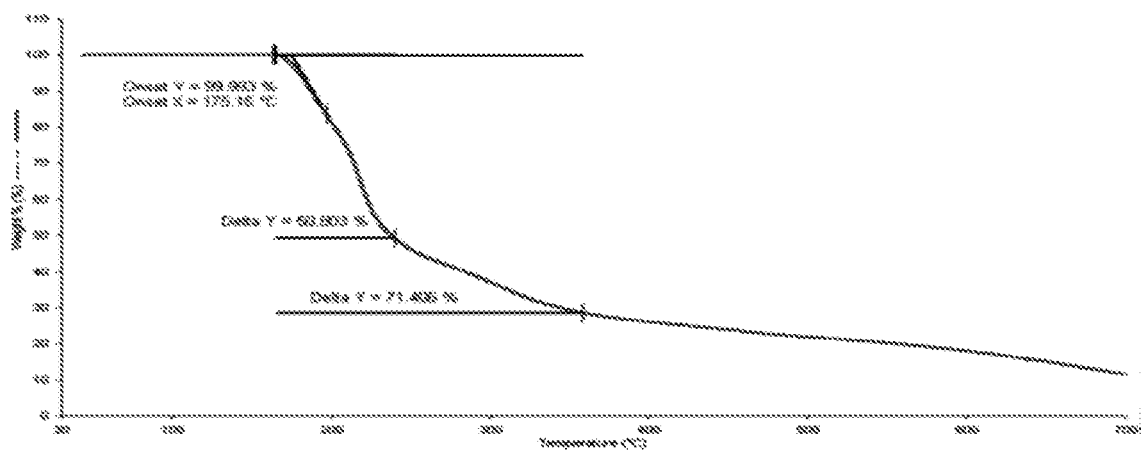
FIG. 6 shows TGA of co-crystals of dichloroacetate tromethamine.

In another embodiment, the present invention provides co-crystals of dichloroacetate tromethamine characterized by TGA as shown in FIG. 6.

In one embodiment, the present invention provides process for the preparation of novel crystalline form dichloroacetic acid tromethamine salt.

In another embodiment, reaction conditions used to novel crystalline form dichloroacetic acid tromethamine salt is cooling the reaction mixture <10° C. for more than 2 to 6 hours or longer to obtain pure and stable crystals.

The present invention provides process for the preparation of novel tromethamine salt haloacetic acid of Formula (I)

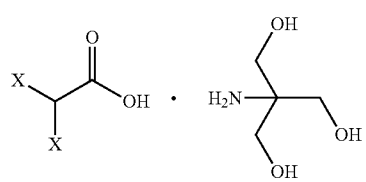
(I)

which comprises combining haloacetic acid of Formula (IV)

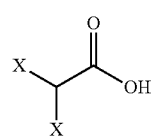
(IV)

and tromethamine of Formula (III) in water or organic solvent

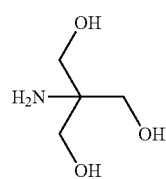
(III)

wherein X is selected from chloro, bromo, fluoro and iodo.

In a preferred embodiment, the present invention provides a process for preparing haloacetic acid salt of Formula (I)

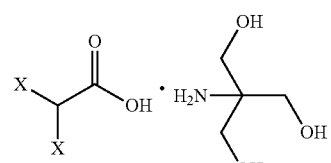
(I)

a) combining haloacetic acid and tromethamine in water or organic solvent,
b) stirring the reaction mixture of step (a) for 10 to 30 min at room temperature then heating the reaction mixture from step (b) at 50 to upto reflux temperature of solvent to obtain haloacetic acid tromethamine salt,
c) isolating the haloacetic acid tromethamine salt,
d) drying the product.

In another embodiment, the present invention provides a process of crystalline form of haloacetic acid salt of Formula (I)

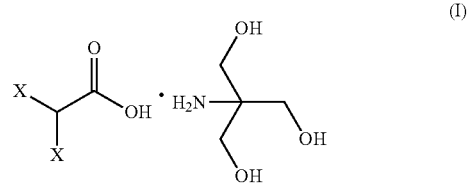
(I)

a) combining haloacetic acid and tromethamine in water or organic solvent,
b) stirring the reaction mixture of step (a) for 10 to 30 min at room temperature then cooling the reaction mixture from step (b) at <10° C. for more than 2 to 6 hours or longer to obtain pure and stable crystals,
c) isolating the crystalline form of haloacetic acid tromethamine salt,
d) drying the product.

The present invention provides process for the preparation provides novel tromethamine salt of dichloroacetic acid of Formula (II)

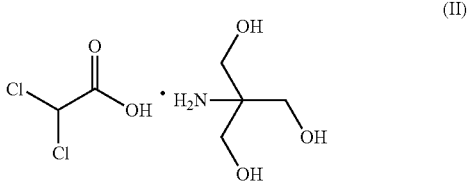 [SMILES: O=C(O)C(Cl)Cl ; NC(CO)(CO)CO]
(II)

which comprises combining dichloroacetic acid of Formula (V)

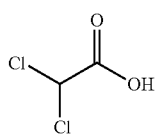
(V)

and tromethamine of Formula (III) in water or organic solvent.

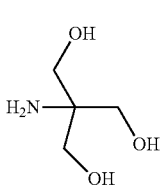
(III)

In yet another preferred embodiment, the present invention provides a process novel tromethamine salt of dichloroacetic acid of Formula (II)

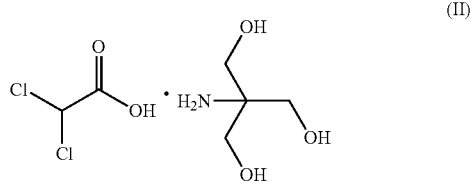 [SMILES: O=C(O)C(Cl)Cl ; NC(CO)(CO)CO]

(II)

a) combining dichloroacetic acid and tromethamine in water or organic solvent,
b) stirring the reaction mixture of step (a) for 10 to 30 min at room temperature then heating the reaction mixture from step (b) at 50 to upto reflux temperature of the solvent to obtain dichloroacetic acid tromethamine salt,
c) isolating the dichloroacetic acid tromethamine salt,
d) drying the product.

In a preferred embodiment, the present invention provides a process of crystalline form of dichloroacetate tromethamine salt of Formula (II)

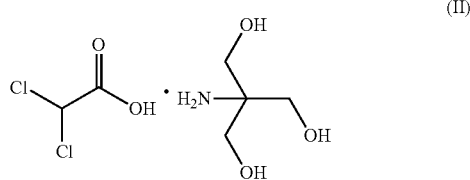 [SMILES: O=C(O)C(Cl)Cl ; NC(CO)(CO)CO]

(II)

a) combining dichloroacetic acid and tromethamine in water or organic solvent,
b) stirring the reaction mixture of step (a) for 10 to 30 min at room temperature then cooling the reaction mixture from step (b) at <10° C. for more than 2 to 6 hours or longer to obtain pure and stable crystals. Salt precipitates as clear crystalline form,
c) isolating the crystalline form of dichloro acetic acid tromethamine salt,
d) drying the product.

The powder X-ray diffraction (PXRD) pattern of co-crystals of dichloroacetate tromethamine (FIG. 1) shows very sharp peaks, suggesting that the sample is highly crystalline. The powder X-ray diffraction (PXRD) pattern was measured on Philips X'pert MPD System.

A crystal of $C_4H_{12}NO_3$, $C_2HO_2Cl_2$ (tromethamine dichloroacetate), approximate dimensions 0.240 mm×0.330 mm×0.410 mm, was used for the X-ray crystallographic analysis. The X-ray intensity data were measured on a Bruker D8 VENTURE Kappa Duo PHOTON II CPAD diffractometer equipped with Incoatech multilayer mirrors optics. The intensity measurements were carried out with Mo micro-focus sealed tube diffraction source (MoKα=0.71073 Å) at 297(2) K temperature. The X-ray generator was operated at 50 kV and 1.4 mA. A preliminary set of cell constants and an orientation matrix were calculated from three sets of 36 frames. Data were collected with ω scan width of 0.5° at different settings of φ and 2θ with a frame time of 10 secs keeping the sample-to-detector distance fixed at 5.00 cm for 6 hours. The X-ray data collection was monitored by APEX3 program (Bruker, 2016). 1 All the data were corrected for Lorentzian, polarization and absorption effects using SAINT and SADABS programs (Bruker, 2016). SHELX-97 was used for structure solution and full matrix least-squares refinement on $F^2$. Hydrogen atoms bound to carbon and nitrogen atoms were placed in a geometrically idealized positions and constrained to ride on its parent atoms except the H atom connected to hydroxyl moieties, which was located in the difference Fourier and refined isotropically. An ORTEP III[3] view of compound was drawn with 50% probability displacement ellipsoids and H atoms are shown as small spheres of arbitrary radii.

Co-crystals of dichloroacetate tromethamine is characterised by X-ray crystallographic analysis, with approximate crystal parameters as follows:

| | |
|---|---|
| Crystallographic system | Monoclinic |
| Spatial group | $P2_1$ |
| Crystal size | 0.410 × 0.330 × 0.240 mm$^3$ |
| Cell dimension | a = 8.600(2) Å    α = 90° |
| | b = 6.1391(15) Å   β = 96.982(10)° |
| | c = 9.786(2) Å    γ = 90° |
| Volume | 512.8(2) Å$^3$ |
| Z, calculated density | 1.619 mg/m$^3$ |

$^1$H NMR for co-crystals of dichloroacetate tromethamine shows absence of peak at 12 ppm for COOH of dichloroacetic acid indicates salt formation as shown in FIG. 3. The $^1$H NMR data were measured on Bruker 400 MHz Solution NMR spectrometer equipped with 5 mm BBO probe in DMSO.

$^{13}$C NMR for co-crystals of dichloroacetate tromethamine $^{13}$C NMR shows peaks related to carbonyl of DCA at 166.98 ppm and tromethamine carbons at 59.69 ppm, 61.60 ppm & 70.59 ppm as shown in FIG. 4. The $^{13}$C NMR data were measured using Bruker 400 MHz Solution NMR spectrometer equipped with 5 mm BBO probe in DMSO.

DSC for novel co-crystals of dichloroacetate tromethamine shows solid to liquid transition which starts at 156° C. and completes at 250° C. There are two species which melts at 172° C. and 222° C. Crystalline dichloroacetic acid tromethamine salt is thermally stable upto 150° C. The presence of two species can also be seen the degradation curve. First degrades at 250° C. (53% weight loss) and other degradation completes at 355° C. (8% weight loss). The 100% weight loss is observed around 840° C. Presence of two different peaks in the DSC represents the formation of two different species as shown in FIG. 5. DSC measurements were carried out using STA 6000 (Simultaneous Thermal Analyzer TG with DSC/DTA).

TGA for co-crystals of dichloroacetate tromethamine shows no loss of weight up to 150° C. indicates absence of water molecule and no glass transition temperature for this compound indicated crystalline nature of dichloroacetic acid tromethamine salt as shown in FIG. 6. TGA measurements were carried out using STA 6000 (Simultaneous Thermal Analyzer TG with DSC/DTA).

Yet another preferred embodiment, the present invention provides use of novel salt of dichloroacetate tromethamine for the treatment of various diseases and/or disorders.

In yet another preferred embodiment, the present invention provides stable, water soluble white crystals of dichloromethane tromethamine which overcomes hygroscopicity problem of existing sodium and potassium salts of dichloroacetic acid.

In one embodiment, novel crystalline dichloroacetic acid tromethamine salt of the present invention may be administrated orally, rectally, vaginally, intranasally, locally (including intraoccularly, intraorally and sublingually) or parenterally (including subcutaneously, intramuscularly, intravenously, intradermally, intrathecally and epidurally), etc.

In another embodiment, novel crystalline dichloroacetic acid tromethamine salt of the present invention can be administered alone but will generally be administered in admixture with a suitable pharmaceutical excipient, diluent or carrier selected with regard to the intended route of administration and standard pharmaceutical practice.

In another embodiment, the preferable dosage form for novel crystalline dichloroacetic acid tromethamine salt of the present invention is a tablet, capsule, powder, granule, syrup, suspension, dispersion, emulsion, dropping pill, pulvis, bolus, tincture or cataplasm. A preferable tablet is a conventional tablet, dispersible tablet, effervescent tablet, immediate-release tablet, sustained-release tablet, controlled-release tablet or enteric-coated tablet. A preferable capsule is a conventional capsule, sustained-release capsule, controlled-release capsule or enteric-coated capsule. The novel crystalline dichloroacetic acid tromethamine salt may also be administered as fast-dispersing or fast-dissolving dosage forms or in the form of high energy dispersion or as coated particles.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

The tablets may be manufactured by a standard process, for example, direct compression or a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, novel crystalline dichloroacetic acid tromethamine salt may be combined with various sweetening or flavouring agents, colouring matter or dyes, with emulsifying and/or suspending agents and with diluents such as water, ethanol, propylene glycol and glycerin, and combinations thereof.

In another embodiment, the novel crystalline dichloroacetic acid tromethamine salt of present invention can also be formulated for administration parenterally, for example, intravenously, intra-arterially, intraperitoneally, intrathecally, intraventricularly, intraurethrally, intrasternally, intracranially, intramuscularly or subcutaneously, or it may be administered by infusion or needleless injection techniques.

In another embodiment, the novel crystalline dichloroacetic acid tromethamine salt of present invention can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas.

In one embodiment, the novel crystalline dichloroacetic acid tromethamine salt of present invention can be administered in the form of a suppository or pessary, or it may be applied topically in the form of a gel, hydrogel, lotion, solution, cream, ointment or dusting powder. It may also be dermally or transdermally administered, for example, by the use of a skin patch. It may also be administered by the pulmonary or rectal routes.

In another embodiment, the novel crystalline dichloroacetic acid tromethamine salt of present invention may also be administered by the ocular route, particularly for treating diseases of the eye. For ophthalmic use, the compound can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, it may be formulated in an ointment such as petrolatum.

Pharmacological Data:

The inventiveness of the instantly claimed compound is further evidenced by the comparative biological data showing that the compound of the present invention is superior to sodium dichloroacetate. In particular, experiments have been carried out with Formula (VII) and Formula (VI), whose structures are shown below:

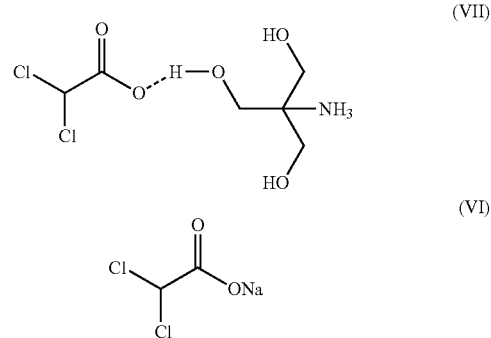

The study was carried out in group sizes of 6 adult fish. Fish were induced with tumor through xenotransplantation of log phase cells. Groups were treated with compounds through oral dosing and treated groups were compared to vehicle treated, to quantify activity against tumor.

Fishes were anesthetized using cold water of 15° C. and 3 ul of $1\times10^6$ log phase MCF7 cells were injected into the peritoneum to induce tumor. Fish were transferred to housing tanks and maintained for 21 days until tumor reached maximum growth phase.

The stock compound is prepared by dissolving appropriate amount of compound in 1 ml of Phosphate Buffered Saline (PBS—8 g of NaCl, 0.2 g of KCl, 1.44 g of $Na_2HPO_4$ and 0.24 g of $KH_2PO_4$ is made to 1 litre and pH adjusted to 7.4.) containing 20% DMSO and 30% fish feed grade coconut oil and stored at 4° C. until use.

Fishes were dosed by mixing the compound with feed for 14 days. A per day dosing weight of compound was dissolved in 3 ul of compound dissolving medium and added to a pellet. The pellets were dried at 70 degrees to remove moisture prior to adding compound and post addition and absorption of compound the pellets were transferred to 4° C.

Statistical comparisons were made using GraphPad. Student's t test with a 95% confidence interval was performed using a two-way ANOVA at an alpha=0.05 (95% confidence interval). Significance is denoted with asterisks: ns not significant, *P<0.05, P<0.01, *P<0.001, ****P<0.0001.

Figure 7:
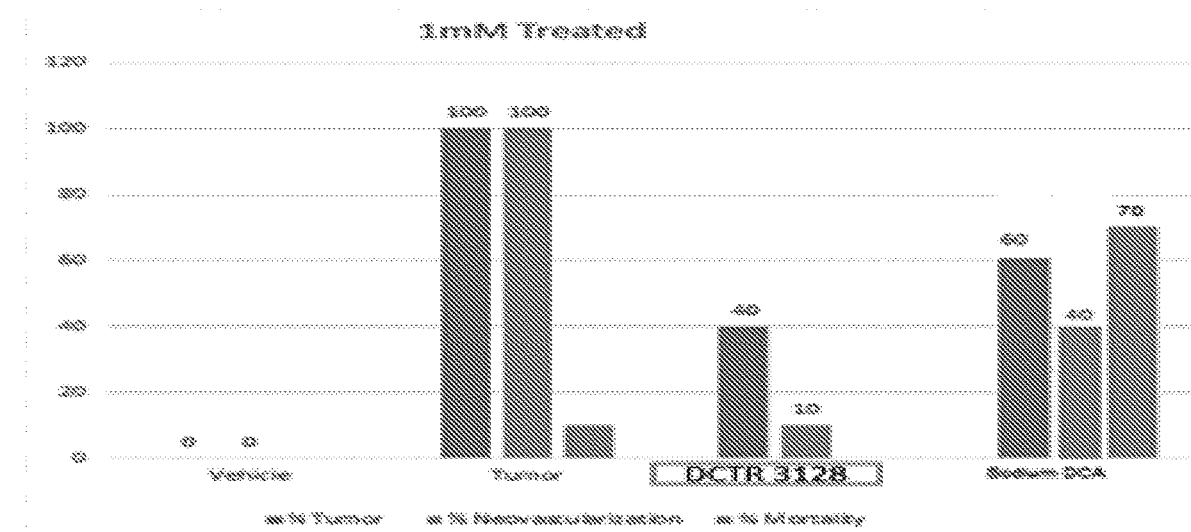
FIG. 7 shows the effect of co-crystals of dichloroacetate tromethamine of 1 mM concentration as compared to sodium dichloroacetate in zebrafish model of hepatocarcinoma.

Co-crystals of dichloroacetate tromethamine Formula (VII) has shown upto 60% of tumor reversal and upto 90% of relative neovascularization reversal in zebrafish model of hepatocarcinoma when treated with 1 mM concentration whereas sodium dichloroacetate of Formula (VI) has shown 40% tumor reversal however only 60% of neovascularization is reversed. No mortality is seen with dichloroacetate tromethamine salt whereas 70% mortality seen in sodium dichloroacetate group as shown in FIG. 7.

Figure 8:
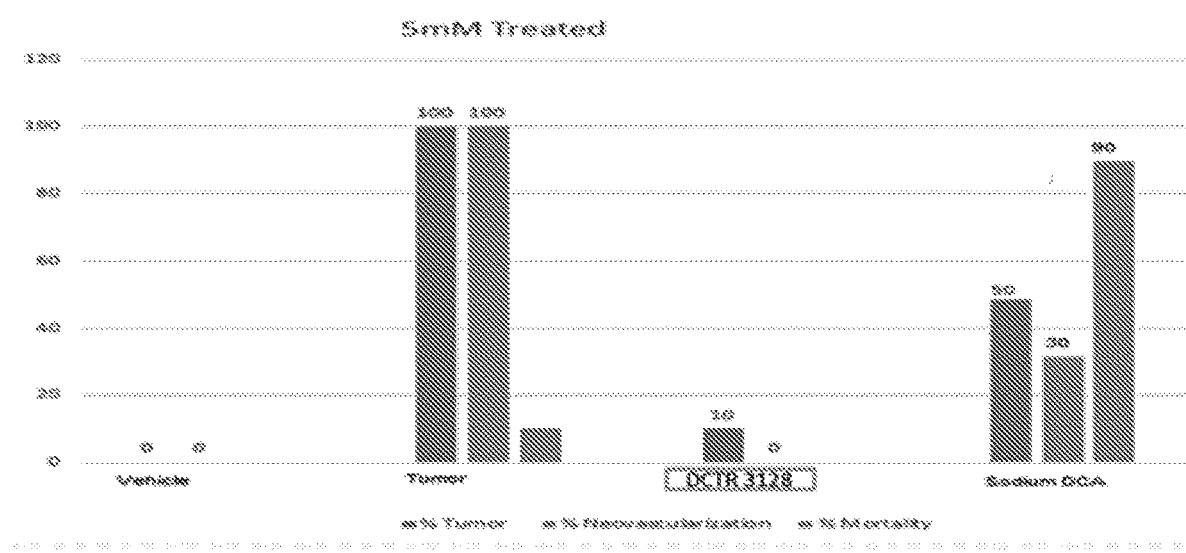
FIG. 8 shows the effect of novel co-crystals of dichloroacetate tromethamine of 5 mM concentration as compared to sodium dichloroacetate in zebrafish model of hepatocarcinoma.

Co-crystals of dichloroacetate tromethamine Formula (VII) has shown up to 90% of relative tumor reversal and complete neovascularization reversal in zebrafish model of hepatocarcinoma when treated with 5 mM concentration whereas sodium dichloroacetate of Formula (VI) has shown 50% tumor reversal and 70% neovascularization reversal. No mortality seen in dichloroacetate tromethamine salt group in 14 days treatment, however very high mortality (90%) seen in sodium dichloroacetate group as shown in FIG. 8.

The present invention is further illustrated by the following examples which are provided merely to be exemplary of the inventions and is not intended to limit the scope of the invention. Certain modifications and equivalents will be apparent to those skilled in the art and are intended to be included within the scope of the present invention.

EXAMPLES

Example 1: Preparation of Tromethamine Dichloroacetate Salt

Anhydrous dichloroacetic acid (V) (1.28 g, 1.2894 mmol) was mixed in water (10 ml) at 25° C. and tromethamine (III) (1.2 g) was dissolved in water (10 ml). 10 ml of aqueous anhydrous dichloroacetic acid and 10 ml of aqueous tromethamine were mixed and stirred continuously for 30 min or more at 50 to upto reflux temperature leading to slow evaporation. Obtained clear concentrated solution was kept for refrigeration at 2 to 8° C. for 5 to 15 hours to obtain salt of tromethamine dichloroacetate which is characterized by TGA, $^1$H NMR & $^{13}$C NMR.

Example 2: Preparation of Powdered Form of Tromethamine Dichloroacetate

Dichloroacetic acid (V) (1.28 g, equimolar) was added to water (10 ml) and the solution is added to one molar tromethamine (III) solution (1.22 g in 10 ml water). Solution is heated to 100° C. until evaporated and salt is precipitated as thin layer sticking to wall of the beaker. The layer is scrapped from inner surface with help of spatula. The off white powdered salt is obtained.

Example 3: Preparation of Crystalline Form of Dichloroacetate Tromethamine

Mixture of dichloroacetic acid (V) (1.28 g, 1.2894 mmol) and tromethamine (DI) (1.2 g) are dissolved in 10 ml of 95% ethanol. The mixture is cooled at 4° C. and evaporated the solvent to obtain precipitate of water soluble white crystalline salt of dichloroacetate tromethamine.

Example 4: Preparation of Crystalline Form of Dichloroacetate Tromethamine

Mixture of dichloroacetic acid (V) (1.28 g, 1.2894 mmol) and tromethamine (III) (1.2 g) are dissolved in 50% ethanol-50% ether mixture. The mixture is cooled at 4 to 10° C. and evaporated the solvent to obtain precipitate of water soluble white crystalline salt of dichloroacetate tromethamine.

Example 5: Preparation of Crystalline Form of Dichloroacetate Tromethamine

Mixture of dichloroacetic acid (V) (1.28 g, 1.2894 mmol) and tromethamine (III) (1.2 g) are dissolved in 20 ml of ether. The mixture is cooled at 4° C. and evaporated the solvent to obtain precipitate of water soluble white crystalline salt of dichloroacetate tromethamine.

Example 6: Preparation of Crystalline Form of Dichloroacetate Tromethamine

Mixture of dichloroacetic acid (V) (0.64 gm) and tromethamine (III) (0.6 g) are dissolved in 25 ml of acetone. The mixture is cooled and evaporated the solvent to obtain precipitate of water soluble white crystalline salt of dichloroacetate tromethamine.

We claim:

1. A tromethamine salt of haloacetic acid co-crystal, wherein the tromethamine salt of haloacetic acid co-crystal is a co-crystal of tromethamine dichloroacetate salt of Formula (VII)

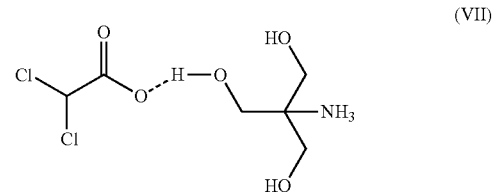

(VII)

characterized by single crystal X-ray data $C_6H_{13}Cl_2NO_5$ (M=250.07 g/mol): monoclinic, space group $P2_1$, a=8.600 (2) Å, b=6.1391(15) Å, c=9.786(2) Å, α=90°, β=96.982 (10°), γ=90°, V=512.8(2) Å$^3$, Z=2, T=297(2) K, μ(Mo Kα)=0.630 mm$^{-1}$, Dcalc=1.619 Mg/m$^3$, 12616 reflections measured)(2.386≤2θ≤33.105°), 3782 unique ($R_{int}$=0.0216, $R_{sigma}$=0.0229), wherein final $R_1$ was 0.0175 (I>2σ(I)) and $wR_2$ was 0.0435.

2. The tromethamine salt of haloacetic acid co-crystals as claimed in claim 1, wherein the co-crystals of dichloroacetate tromethamine of Formula (VII) are characterized by Powder x-ray diffraction pattern comprising diffraction peaks at 8.1, 12.8, 14.1, 17.1, 18.1, 19.1, 19.3, 21.2, 23.2, 24.5, 25.3, 26.0, 27.0, 28.0, 29.8, 30.2, 31.0, 34.0, 35.2, 36.0, 41.20, 42.0, 44.0 and 45.0 0.2 degrees 2 theta.

3. The tromethamine salt of haloacetic acid co-crystals as claimed in claim 1, wherein the co-crystals of dichloroacetate tromethamine of Formula (VII) are characterized by two endotherms at 172° C. and 222° C.

4. The tromethamine salt of haloacetic acid co-crystals as claimed in claim 1, wherein the tromethamine and dichloroacetic acid are in the ratio of 1:1 to 1:3.

* * * * *